United States Patent [19]

Langdon

[11] 4,265,774

[45] May 5, 1981

[54] OXYALKYLATED POLYGLYCEROLS AND WATER-BASED LUBRICANTS PREPARED THEREFROM

[75] Inventor: William K. Langdon, Grosse Ile, Mich.

[73] Assignee: BASF Wyandotte Corporation, Wyandotte, Mich.

[21] Appl. No.: 736,948

[22] Filed: Oct. 29, 1976

[51] Int. Cl.$^3$ .............................................. C10M 1/06
[52] U.S. Cl. .................................. 252/49.3; 252/49.7; 252/52 A; 568/851; 568/852
[58] Field of Search .................. 252/49.3, 49.7, 52 A; 260/615 B

[56] References Cited

U.S. PATENT DOCUMENTS

| | | | |
|---|---|---|---|
| 2,552,532 | 5/1951 | Groote | 260/615 B |
| 2,674,619 | 4/1954 | Lundsteel | 260/615 B |
| 2,733,272 | 1/1956 | Horsley et al. | 252/52 R |
| 2,944,982 | 7/1960 | Groote et al. | 260/615 B |
| 3,519,559 | 7/1970 | Quinlan | 260/615 B |
| 3,899,387 | 8/1975 | Freis et al. | 260/615 B |
| 3,925,216 | 12/1975 | Moorhouse | 252/49.3 |
| 4,061,684 | 12/1977 | Helfert et al. | 252/52 A |

*Primary Examiner*—Andrew Metz
*Attorney, Agent, or Firm*—Joseph D. Michaels

[57] ABSTRACT

High molecular weight polyglycerol derivatives, useful as thickening agents for water-based lubricants, are prepared by oxyalkylating a polyglycerol with ethylene oxide or a mixture of ethylene oxide and propylene oxide. The polyglycerol derivatives are characterized as having an average of more than five glycerol units, and in having more than 95% and preferably more than 99% alkylene oxide units. These compounds exhibit excellent shear strength and provide an improved hydrolube when incorporated therein.

4 Claims, No Drawings

4,265,774

OXYALKYLATED POLYGLYCEROLS AND WATER-BASED LUBRICANTS PREPARED THEREFROM

BACKGROUND OF THE INVENTION

1. Field of the Invention

The present invention relates to oxyalkylated polyglycerols and water-based lubricants prepared therefrom. These lubricants have excellent shear strength stability.

2. Description of the Prior Art

It is known to oxyalkylate glycerol, and U.S. Pat. No. 2,733,272 discloses oxyalkylating glycerol with mixtures of ethylene oxide and propylene oxide. The ratio of ethylene oxide to propylene oxide is 20:80 to 80:20 with 1:1 being preferred and a very broad area of use is specified. However, the molecular weight range is a maximum of 5,000 to 6,000 which is way below the desired value for the thickening agents of the present invention. In addition, the glycerol base does not provide the advantages obtained by polyglycerol bases.

It is also known to oxyalkylate polyglycerols such as diglycerols and triglycerols. For example, U.S. Pat. No. 3,110,737 discloses oxyalkylating with a mixture of butylene oxide and ethylene oxide, and U.S. Pat. No. 2,679,520 shows oxypropylating lower polyglycerols and then making esters therefrom. In both cases, the higher polyglycerols are rejected, and the patentees are making water-insoluble products. Therefore, the patentee's products are not suitable as thickening agents for hydrolubes.

SUMMARY OF THE INVENTION

In accordance with the present invention, there is provided a mixture of compounds having the formula:

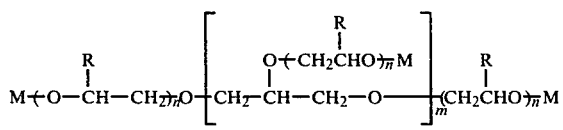

where R is hydrogen or a methyl group and in which at least 75% of the R groups are hydrogen, M is hydrogen or an alkali metal, m is an integer having an average value greater than 5, and n is an integer having an average value high enough to provide a compound mixture having greater than 95% alkylene oxide moieties and preferably more than 99% alkylene oxide moieties. This composition is characterized by having an excellent shear strength and it is useful as a thickening agent in water-based lubricants.

The composition is prepared by reacting a polyglycerol with ethylene oxide or a mixture of ethylene oxide and propylene oxide in the presence of an alkali catalyst. Conveniently, the alkylene oxide is added in stages, and the addition is continued until the desired molecular weight is obtained. If desired, at one or more of the stages, ethylene oxide or propylene oxide can be added individually to form one or more homopolymer blocks, provided the amount of oxypropylene does not exceed 25% of the oxyalkylene total. Preferably, the addition is such that the polyglycerol moiety in the final product is less than 1%.

Thus it is seen that a wide range of molecular weights and corresponding viscosities may be obtained, and the most preferred compositions have a molecular weight above about 20,000. It is also believed that these compositions have good lubricity and wear characteristics.

In accordance with the invention, hydrolubes are also prepared, and these hydrolubes have excellent shear strength. Typically, the hydrolubes are prepared utilizing water and the compositions of the invention as thickening agents together with the usual small amounts of additives such as corrosion inhibitors. In view of the high viscosities obtainable in the compositions of this invention, relatively small amounts of thickener may be used. Accordingly, a hydrolube prepared in accordance with the invention will contain, say, from 2 to 20% of the composition described above.

DESCRIPTION OF THE PREFERRED EMBODIMENTS

The first step in the preparation of the composition of the invention is the preparation of a polyglycerol containing a desired average number of glycerol units. This step may be performed in any suitable manner, as is well known to those skilled in the art. One satisfactory procedure, involving dehydration of glycerol in the presence of an alkaline catalyst at 100° C. to 300° C. is adequately disclosed in Babayan et al, U.S. Pat. No. 3,637,774, the disclosure of which is hereby incorporated by reference.

It is important that the number of glycerol units to be at least 5 and typically the number will be from 5 to 30 units. The use of a large nucleus of polyglycerol units provides for a large number of reactive hydroxyl sites and, correspondingly, more chains of alkylene oxide units. In this way relatively high molecular weights may be obtained with relatively short chains, and it is believed that the excellent shear characteristics of the compositions of this invention are due to this geometry. While a minimum of 5 glycerol units provides good compositions, especially good results are obtained by using polyglycerols having more than 10 glycerol units.

In general, the alkylene oxide chains may be added to the hydroxyl groups of the polyglycerol by any of the known techniques using any of the known catalysts for such reaction. I have found that the reaction proceeds very smoothly by utilizing alkali catalysts such as potassium hydroxide and sodium hydroxide. The oxyalkylation reaction is conveniently carried out under heat and pressure, typically 125° C. and 6-8 atmospheres pressure. The alkylene oxide is preferably added in stages, and the reaction product may be divided into aliquots during the addition, if desired. For example, the preferred area of the invention provides for the alkylene oxide units to be more than 99% of the composition, and in a preferred product, the ratio of polyglycerol units to alkylene oxide units is 1:216 by weight. Thus volume considerations make a division into aliquots quite practical.

It has been found that the reaction may be continued to provide high molecular weight product, and compositions having an average molecular weight above about 20,000 are especially useful.

These compositions are especially useful as a thickener in hydrolubes, and hydrolubes incorporating these compositions are within the ambit of this invention. In general, the hydrolube will contain from about 2–20% and preferably from about 5–15% of the composition of this invention. A typical composition, then, consists essentially of, say, 2–20% by weight thickener, 1–3% by weight additives and 62–92% by weight water. Typical additives include corrosion inhibitors such as mercaptobenzothiazole, fatty acids, alkali, potassium hydroxide, potassium nitrate, and morpholine.

Hydrolube compositions prepared as just described have been tested for shear strength by measuring the viscosity before and after repeated test cycles under high pressure. These tests have shown that the compositions have excellent shear strength characteristics.

The invention described above is more fully illustrated in the following specific examples, in which parts are by weight unless otherwise indicated. The examples are to be interpreted as illustrative only and not in a limiting sense.

EXAMPLE 1

A polyglycerol containing an average of 5.4 glycerol units is reacted with a mixture of ethylene oxide and propylene oxide in an 85:15 weight ratio.

Part A: Preparation of Polyglycerol

To a 2-liter, four-neck flask having a stirrer, nitrogen inlet, thermometer and distillation take-off head, there are added 1840 grams (20 moles) of glycerol and 225 grams (2 moles) of 50% potassium hydroxide. The mixture is heated at atmospheric pressure under a nitrogen blanket to remove water in the potassium hydroxide solution and water of condensation produced in the formation of the polyglycerol. After 120 minutes, the pot temperature is 237° C. and 212 milliliters of distillate is collected. The weight of polyglycerol residue is 1544 grams. After standing overnight, the product is heated to 110° C. at 2 millimeters of mercury to strip volatiles. The weight of the stripping is 12.5 grams. Analysis of a product prepared according to this procedure indicated the hydroxyl number of the product to be 996, which corresponds to an average of 5.4 glycerol units.

Part B: Oxyalkylation Reaction

Oxyalkylation with an 85:15 weight mixture of ethylene oxide:propylene oxide is carried out in a one-gallon autoclave in three stages at a reaction temperature of 125° C. and a pressure of approximately 90 psig. The charge for the first stage is 400 grams of the polyglycerol of 5.4 units as prepared above and 2,400 grams of an 85:15 weight mixture of ethylene oxide:propylene oxide. Thus, the weight ratio of alkylene oxides to polyglycerol is 6:1. At each of the reaction stages, 400 grams of the product of the preceding stage is charged along with 2,400 grams of an 85:15 weight mixture of ethylene oxide:propylene oxide. Thus the final weight ratio of alkylene oxides to polyglycerol is 216:1. Analysis of a product prepared according to this procedure indicated a hydroxyl number of 7.1, which corresponds to an equivalent weight of 7,900. Gel permeation chromatography, using polystyrene as a standard, indicated the peak molecular weight to be 42,000, and the average molecular weight to be 24,800.

EXAMPLE 2

A polyglycerol containing an average of 13.5 glycerol units is reacted with a mixture of ethylene oxide and propylene oxide in an 85:15 weight ratio.

Part A: Preparation of Polyglycerol

To an apparatus, similar to that described in Example 1, are added 2,760 grams of glycerol (30 moles) and 55.2 grams of 50% NaOH. The mixture is heated at a pressure of approximately 225 millimeters with the temperature being gradually raised to remove water. A total of 598 grams of aqueous fraction are taken off over a reaction time of 10 hours at a maximum temperature of 246° C. Polyglycerol having a hydroxyl number of 885 which corresponds to an average molecular weight of 1,022 and 13.5 glycerol units is obtained in an amount of 2,193 grams.

Charge stock for Part B is prepared by taking 955 grams of the polyglycerol, adding 115 grams of 50% potassium hydroxide, and stripping at approximately 3 millimeters of pressure up to 140° C. to remove water and form potassium alkoxide. Since the polyglycerol contains 1% of sodium hydroxide, the amount of combined alkali is approximately 7%.

Part B: Oxyalkylation Reaction

A 400-gram aliquot of the polyglycerol catalyst mixture is charged to a 1-gallon autocalve and reacted in three stages with 2,400 grams of 85:15 ethylene oxide:-propylene oxide in each stage as described in Example 1 above. Analysis of a product prepared according to this procedure indicated a hydroxyl number of 5.7, which corresponds to an equivalent weight of 9842. Gel permeation chromatography indicated the peak molecular weight to be 53,000, and the average molecular weight to be 22,000.

EXAMPLE 3

A polyglycerol containing an average of 12 glycerol units is reacted with ethylene oxide.

Part A: Preparation of Polyglycerol

One hundred forty moles (12,880 grams) of glycerol and 259 grams of 50% sodium hydroxide are charged to a 12-liter flask and heated at approximately 240° C. at 300 millimeters of mercury for 25 hours. The weight of the honey-like viscous product obtained is 10,312 grams, which corresponds to 80% of the glycerol charge. The hydroxyl number of the product obtained is 865, which corresponds closely with dodecaglycerol. Dodecaglycerol has a hydroxyl number of 868 and a molecular weight of 906. The hydroxyl functionality of this product would be 14.

Part B: Oxyethylation Reaction

Four hundred grams of the polyglycerol-catalyst mixture of Part A is charged to a one-gallon autoclave and reacted with 2,400 grams of ethylene oxide at a temperature of 125° C. and a pressure of approximately 110 psig. A 600-gram aliquot of the above first stage ethoxylated product is treated with 36 grams of 50% potassium hydroxide and this mixture is stripped up to 135° C. at 3 millimeters of mercury. The weight of the stripped material is 612 grams. A 400-gram aliquot of this product is then reacted with 2,400 grams of ethylene oxide in the manner described above. Following this, a 400-gram aliquot of the second stage is reacted with 2,400 grams of ethylene oxide in a third stage. The final product thus obtained has a hydroxyl number of 5.1, which corresponds to an equivalent weight of 11,000 and a molecular weight of 154,000 based on a functionality of 14. At 10% concentration in water, the viscosity was 258 SUS at 100° F.; and at 7.5% concentration, the viscosity was 150 SUS at 100° F.

EXAMPLE 4

A hydrolube is prepared using the compositions of Examples 1-3.

A hydrolube is prepared by adding thickener to deionized water containing the following additives: potassium hydroxide 0.22%, potassium nitrate 1.0%, morpholine 1.28%, lauric acid 0.72%, and mercaptobenzothiazole 0.21%. The compositions of each of the examples is added in the amount indicated in the table below and the hydrolubes thus formed are tested for shear strength by measuring the viscosity of the hydrolube before and after the stress test indicated.

TABLE

| Thickener | Concentration of Thickener | Initial Viscosity (SUS) | Stress | Viscosity (SUS) after Stress |
| --- | --- | --- | --- | --- |
| Example 1 | 15.7% | 277 | 5800 cycles at 1000 psig | 275 |
| Example 2 | 13.0% | 264 | 5800 cycles at 1000 psig | 260 |
| Example 3 | 9.3% | 241 | 5800 cycles at 1000 psig | 227 |

From the above table, it is seen that the hydrolube compositions prepared in accordance with the invention exhibit good thickening ability and excellent resistance to shear at high pressures.

From the foregoing description, it is seen that I have shown and described a new composition suitable as a thickener, and a hydrolube composition utilizing the same. While I have described herein certain embodiments of my invention, I intend to cover as well any change or modification therein which may be made without departing from the spirit and scope of the appended claims.

The embodiments of the invention in which an exclusive property or privilege is claimed are defined as follows:

1. A composition of matter comprising a mixture of compounds having the formula:

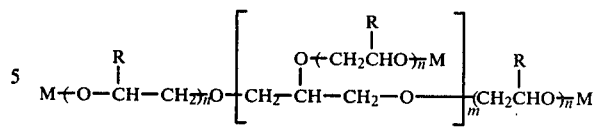

where R is hydrogen or a methyl group and in which at least 75% of the R groups are hydrogen, M is hydrogen or an alkali metal, m is an integer having an average value greater than 5, and n is an integer having an average value high enough to provide a compound mixture having an average molecular weight greater than about 20,000.

2. A composition, as defined in claim 1, in which the alkylene oxide moieties are substantially all ethylene oxide.

3. A hydrolube composition consisting essentially of from about 62 to about 92% by weight of water, from about 1 to about 3% by weight of additives, and from about 2 to about 20% by weight of a mixture of compounds having the formula:

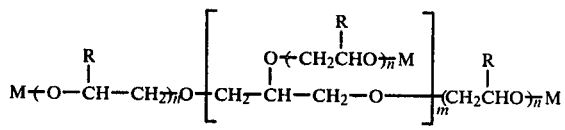

where R is hydrogen or a methyl group and in which at least 75% of the R groups are hydrogen, M is hydrogen or an alkali metal, m is an integer having an average value greater than 5, and n is an integer having an average value high enough to provide a compound mixture having an average molecular weight greater than about 20,000.

4. A hydrolube composition, as defined in claim 3, in which the defined mixture of compounds is present in a range of from about 5 to about 15% by weight.

* * * * *